US009815231B2

(12) United States Patent
Stadler

(10) Patent No.: US 9,815,231 B2
(45) Date of Patent: Nov. 14, 2017

(54) METHOD FOR MANUFACTURING A BREAST PROSTHESIS

(71) Applicant: Amoena Medizin-Orthopadie-Technik GmbH, Raubling (DE)

(72) Inventor: Maximilian Stadler, Prutting (DE)

(73) Assignee: AMOENA MEDIZIN-ORTHOPADE-TECHNIK GMBH (DE)

( * ) Notice: Subject to any disclaimer, the term of this patent is extended or adjusted under 35 U.S.C. 154(b) by 281 days.

(21) Appl. No.: 14/698,957

(22) Filed: Apr. 29, 2015

(65) Prior Publication Data

US 2015/0314493 A1    Nov. 5, 2015

(30) Foreign Application Priority Data

Apr. 30, 2014    (DE) .................. 10 2014 006 313

(51) Int. Cl.
| | |
|---|---|
| B29C 43/20 | (2006.01) |
| B29C 43/12 | (2006.01) |
| A61F 2/12 | (2006.01) |
| A61F 2/52 | (2006.01) |
| B29K 83/00 | (2006.01) |
| B29K 105/24 | (2006.01) |
| B29K 675/00 | (2006.01) |
| B29L 31/00 | (2006.01) |
| B29C 43/18 | (2006.01) |

(52) U.S. Cl.
CPC .............. B29C 43/12 (2013.01); A61F 2/12 (2013.01); A61F 2/52 (2013.01); B29C 43/203 (2013.01); B29C 43/206 (2013.01); A61F 2002/523 (2013.01); B29C 43/183 (2013.01); B29K 2083/005 (2013.01); B29K 2105/24 (2013.01); B29K 2675/00 (2013.01); B29L 2031/7532 (2013.01)

(58) Field of Classification Search
CPC ........................................ B29C 43/12
USPC ............................................... 623/7
See application file for complete search history.

(56) References Cited

U.S. PATENT DOCUMENTS

| | | | | |
|---|---|---|---|---|
| 4,249,975 | A * | 2/1981 | Rechenberg | A61F 2/52 156/245 |
| 5,693,164 | A * | 12/1997 | Chang | A41C 5/005 156/152 |
| 8,608,881 | B2 * | 12/2013 | Smith | A61F 2/5046 156/61 |
| 2002/0193878 | A1 * | 12/2002 | Bowman | A61F 2/52 623/7 |
| 2007/0267131 | A1 * | 11/2007 | Reitmeter | A61F 2/52 156/242 |
| 2013/0096675 | A1 * | 4/2013 | Sjunnesson | A61F 2/5046 623/7 |
| 2015/0190244 | A1 * | 7/2015 | Halley | A61F 2/52 623/7 |

FOREIGN PATENT DOCUMENTS

CA    WO 2010015075 A1 *    2/2010 ........... A61F 2/5046

* cited by examiner

*Primary Examiner* — Cachet Sellman
(74) *Attorney, Agent, or Firm* — Carter, DeLuca, Farrell & Schmidt, LLP

(57) ABSTRACT

A method for manufacturing a breast prosthesis, in which a film bag is welded together from at least three film layers for producing at least two chambers.

15 Claims, 1 Drawing Sheet

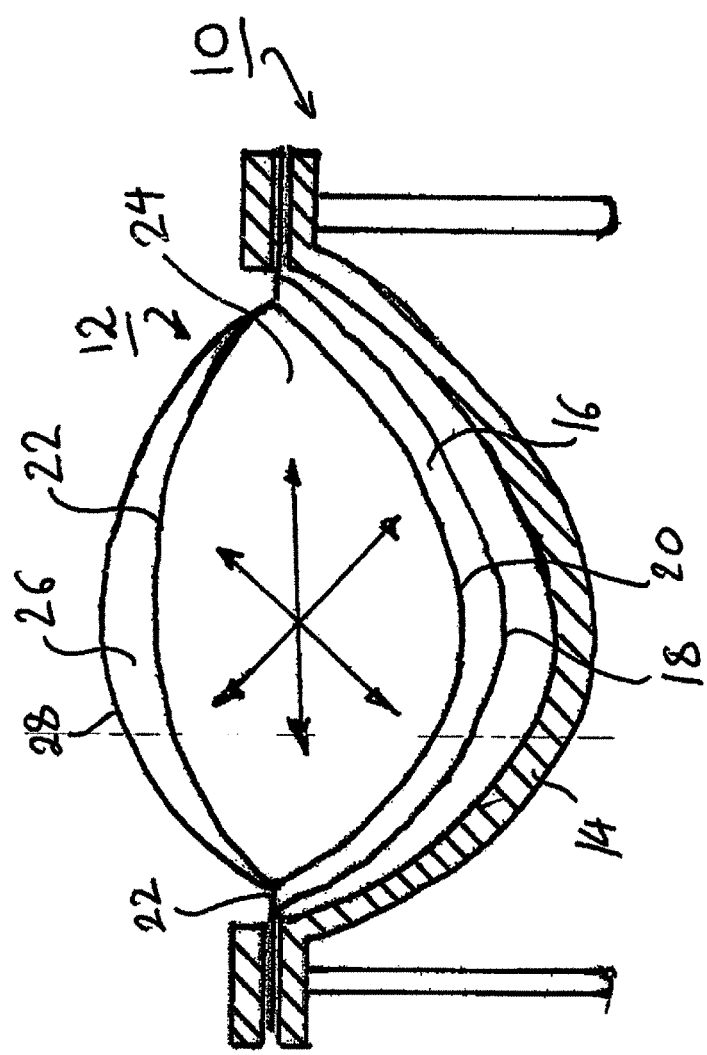

METHOD FOR MANUFACTURING A BREAST PROSTHESIS

CROSS REFERENCE TO RELATED APPLICATIONS

This application claims priority to German Application No. 10 2014 006 313.5, filed Apr. 30, 2014, the entirety of which is hereby incorporated by reference.

BACKGROUND

1) Technical Field

The invention relates to a method for manufacturing a breast prosthesis which substantially consists of bodies modeling the shape of the breast, which are shrink-wrapped in plastic films.

2) Description of Related Art

Breast prostheses are known already, in which these bodies modeling the breast shape consist of a transparent addition crosslinking two-component silicone-rubber compound. Since the silicone material is transparent by nature, the desired skin color is achieved by addition of small amounts of color pigments—for example by admixture of 0.2 wt-% of color pigment. Typically, polyurethane films are used as films enclosing the silicone. The same have a high elasticity and softness. Nevertheless, they are rather stiff as compared to the silicone used, so that the film tends to form wrinkles. Due to the transparency of the polyurethane film and the silicone, these wrinkles however are not clearly visible and therefore do not disturb.

By adding hollow spherical fillers which are used for weight reduction of the breast prostheses, a strongly covering white color is obtained in the lightweight silicone. This results from the fact that the hollow spherical fillers consist of a multitude of spheres which individually act as color prism. This phenomenon for example is comparable with transparent snow crystals which due to the refraction of light in sum likewise appear white. By addition of color pigments, the white color of the lightweight silicone can be changed in direction of an adaptation to the skin color. However, this is not reproduced as natural as it is possible with standard silicone. Due to these differences in color, the aforementioned wrinkles of the polyurethane film become much more visible due to the opaque color of the lightweight silicone and optically are perceived as disturbing.

To avoid the aforementioned problem, it has become known already to create a multilayer breast prosthesis, wherein on the outside a thin covering layer of standard silicone is formed on the front side, which is transparent and with the coloring adapted to the skin color provides an attractive appearance. From EP 0 880 951 B1 there is known a method for manufacturing a multi-chamber breast prosthesis, in which the manufacture of this so-called cosmetic layer is effected outside the prosthesis mold. In this known method it is disadvantageous that the cosmetic layer produced outside the prosthesis mold exhibits differences in thickness, i.e. does not have a uniformly thin outer layer. As a result, the attractive appearance which should be achieved by the comparatively thin covering layer frequently is achieved only insufficiently.

It now is the object of the present invention to develop a method which creates such prosthesis with a so-called cosmetic covering layer with constant thickness.

SUMMARY

The method for manufacturing the breast prosthesis according to the invention, which substantially consists of bodies modeling the shape of the breast, which are shrink-wrapped in plastic films, comprises the following steps:
  welding of a film bag from at least three film layers for producing at least two chambers,
  inserting and fixing the film bag in the prosthesis molding tool,
  filling of the outer chamber with a compound preferably crosslinking already at ambient temperature or at slightly elevated temperature,
  pre-crosslinking of the compound, while at the same time inflating the at least second chamber by means of air or another fluid,
  draining the air or the other fluid from the second chamber and subsequently filling of the at least second chamber with a second compound,
  closing of the prosthesis molding tool, in order to completely crosslink the compounds present in the chambers at elevated temperature.

Corresponding to the invention, the breast prosthesis is manufactured with a very uniformly thin cosmetic covering layer by the pre-crosslinking step included in the aforementioned method and by simultaneously inflating the second chamber or by correspondingly filling the second chamber with another fluid. By previously filling the first chamber, which later on forms the cosmetic covering layer, as well as pre-crosslinking and simultaneously inflating the adjacent second chamber within the prosthesis molding tool it can be ensured that a uniform thin covering layer is formed on the front side of the breast prosthesis.

As soon as the compound filled into the first chamber is pre-crosslinked, the gas or fluid filled into the second chamber can be drained and this chamber can be filled with the corresponding compound, which usually includes lightweight fillers in addition to the crosslinking material. After closing the prosthesis molding tool, the same is heated in a corresponding oven to such an extent that the final shaping of the breast prosthesis is effected by corresponding crosslinkage of the compound filled into the chambers and stretching of the film.

Advantageous aspects of the invention can be taken from the sub-claims following the main claim.

Accordingly, the film bag can be fabricated from four film layers by forming three chambers, wherein the comparatively thin third chamber is arranged on the back of the breast prosthesis and forms the so-called cavity layer, which lies close to the wearer.

Particularly advantageously, the third chamber together with the first chamber is filled with a material which initially likewise is only pre-crosslinked.

The first and possibly the third chamber can form a thin outer layer with a layer thickness of preferably 2 mm-10 mm, which surround the second chamber on one side and possibly on two sides.

The film layers forming the film bag advantageously can be made of polyurethane. The polyurethane films can have a thickness of about 40 μm-100 μm.

The polyurethane films can be welded together by means of thermal welding, HF welding (high-frequency welding) or laser welding. The bodies shrink-wrapped in the plastic films can be made of an addition crosslinking silicone, a thermoplastic polyurethane and/or a thermoplastic elastomer.

The first compound filled into the first chamber of the film bag can consist of a silicone mixture which crosslinks sufficiently strongly already at room temperature, in order to be pre-crosslinked largely dimensionally stable after few minutes of reaction time.

Advantageously, the temperature for the complete crosslinkage of the compound filled into the second chamber of the film bag is chosen such that the film material permanently is plastically deformed without permanently damaging the film. This results in a stretching of the film and a dimensionally accurate lying to the surface of the prosthesis molding tool.

According to another particularly advantageous aspect of the invention, the film layers forming the film bag are welded together by forming a welding seam of uniform width, wherein by choosing the width of the welding seam and choosing the inflation pressure of the second chamber the uniformity of the layer thickness is adjustable.

Advantageously, the welding seam width of the films forming the first chamber is chosen so broad that at a given inflation pressure a uniform layer thickness is formed, while the welding seam of the films forming the third chamber is chosen comparatively narrower, in order to obtain a layer thickness non-uniform across the chamber at the same inflation pressure such that the layer thins out towards the welding seam, while it is thicker towards the center. In a particularly advantageous way, a first cosmetic covering layer can be formed thereby, which has a uniform layer thickness and therefore a good optical effect. On the other hand, the third chamber which forms the cavity layer can be formed thick in the middle for a better distribution of pressure, while it thins out towards the edges. The cavity layer thereby optimally fits snugly to the wearer.

BRIEF DESCRIPTION OF THE DRAWING

Further features, details and advantages of the invention will be explained with reference to an exemplary embodiment illustrated in the drawing. The only FIGURE shows schematic representation of a prosthesis molding tool only shown here in part, into which a prosthesis is inserted at the time of pre-crosslinkage of the outer layers.

DETAILED DESCRIPTION

When manufacturing the breast prosthesis according to the invention, a film bag initially is welded from at least three film layers. As far as three film layers are used, two chambers are formed. Alternatively however, as shown in the FIGURE, four film layers also can be welded to each other, so that three chambers are obtained. The film used is made of polyurethane in a thickness of typically 50 µm-100 µm. The welding of the film layers is effected by thermal welding, HF welding or laser welding. The film bag designated with 12 as a whole is inserted into a prosthesis molding tool 10. In the FIGURE, the prosthesis molding tool 10 only is shown in part. Here, in particular the lower mold part 14 is shown, which defines the shape of the breast to be modeled. The counterpart of the mold, which is placed onto the mold part 14, is not shown here in detail. There is merely shown the corresponding edge of the counter-mold.

The individual films of the film bag initially are not completely welded on the circumference, so that there is still present an inlet opening not shown in detail in the FIGURE for filling in the silicone mixture described in this exemplary embodiment. Via the opening, the first chamber initially is filled, which is designated with 16 and forms a cosmetic covering layer having a thickness of about 2 mm-10 mm.

The film layers 18 and 20 forming this first chamber 16 are welded together by forming a welding seam 22 of uniform or variable width. After the first chamber 16 is filled with an addition crosslinking two-component silicone rubber compound, the same is pre-crosslinked either at ambient temperature or by supplying heat. During this pre-crosslinking step, the second chamber 24 adjoining the first chamber 16 in the exemplary embodiment shown here is inflated with air, which is represented by the double arrows in the FIGURE. Thus, a pressure thereby is exerted on the film 20 and the opposed film 22. Both the welding seam 22 and the inflation pressure of the air pressed into the second chamber 24 leads to a uniform distribution of the layer thickness in the chamber 16 during the pre-crosslinkage of the crosslinking compound. By choosing the width of the welding seam and by choosing the inflation pressure, an optimized result can be achieved with regard to the uniformity of the layer thickness. In the exemplary embodiment shown here a third chamber 26 also is provided on the back of the second chamber 24. This chamber is located on the side facing the body. This third chamber is filled together with the first, outer chamber 16 and pre-crosslinked together with the same, while the second chamber 24 is inflated correspondingly. The third chamber 26, which is formed by the films 22 and 28, has a non-uniform layer thickness in contrast to the first chamber 16. Here, especially the middle region should be formed thick for a better pressure distribution on the body, while the third chamber should thin out towards the edges. This is achieved by the fact that in the region of the welding seam between the films 22 and 28 just no broad welding seam is formed, but that the films 22 and 28 here are welded to each other so as to be tapering directly, as is shown in the FIGURE.

After correspondingly pre-crosslinking the crosslinking compound present in the first chamber 16 and the third chamber 26, the air kept under positive pressure in the second chamber 24 is drained. Subsequently the second chamber 24, which represents the main chamber, is filled. In the present exemplary embodiment a lightweight silicone, i.e. a mixture of silicone and hollow spherical filler here is filled in. Subsequently, the second non-illustrated mold half of the prosthesis molding tool is put on. This mold half is designed such that the prosthesis consisting of three chambers is enclosed. The correspondingly closed mold subsequently is put into a corresponding oven in which the temperature chiefly is chosen according to the softening temperature and the softening times of the polyurethane film forming the bag. The temperature is set such that in the polyurethane film a permanent, plastic deformation is achieved, without the film however being damaged thermally. Usually, temperatures of about 130° C. are set here. At this temperature, the crosslinking materials in the individual chambers crosslink completely.

After this manufacturing step, the prosthesis is removed from the mold and the protruding film is cut off for example with a sharp knife, a pair of scissors or a punching tool.

The invention claimed is:

1. A method for manufacturing a breast prosthesis having bodies modeling the shape of the breast, which are shrink-wrapped in plastic films, comprising the following steps:
   welding of a film bag from at least three film layers for producing at least first and second chambers,
   inserting and fixing the film bag in a prosthesis molding tool,
   filling the first chamber with a first compound capable of crosslinking at ambient temperature or at slightly elevated temperature,
   pre-crosslinking the compound, while inflating the at least second chamber with a fluid, draining the fluid from the second chamber, and subsequently filling the second chamber with a second compound, closing the prosthesis molding tool, and completely crosslinking the compounds present in the chambers at elevated temperature.

2. The method according to claim 1, wherein the film bag is fabricated from four film layers by forming three chambers, wherein a comparatively thin third chamber is arranged on a back of the breast prosthesis.

3. The method according to claim 2, wherein the third chamber and the first chamber are filled with a material which initially is only pre-crosslinked.

4. The method according to claim 3, wherein the first and optionally the third chamber form a thin outer layer with a layer thickness of 2 mm-10 mm, which surround the second chamber on one side.

5. The method according to claim 4 wherein the thin outer layer surrounds the second chamber on two sides.

6. The method according to claim 2, wherein the film layers forming the film bag are welded together by forming a welding seam of uniform width, wherein by choosing the width of the welding seam and choosing an inflation pressure, uniformity of the layer thickness is adjustable.

7. The method according to claim 6, wherein the welding seam width of the films forming the first chamber is chosen so that at a given inflation pressure a uniform layer thickness is formed, while the welding seam of the films forming the third chamber is chosen comparatively narrower, in order to obtain a layer thickness non-uniform across the chamber at the same inflation pressure such that the layer thins out towards the welding seam, while it is thicker towards the center.

8. The method according to claim 1, wherein the film layers forming the film bag are made of polyurethane.

9. The method according to claim 8, wherein the polyurethane film layers have a thickness of 40 μm-100 μm.

10. The method according to claim 1, wherein the film layers are welded together by thermal welding, HF welding or laser welding.

11. The method according to claim 1, wherein the bodies shrink-wrapped in the plastic films are made of an addition crosslinking silicone, a thermoplastic polyurethane and/or a thermoplastic elastomer.

12. The method according to claim 1, wherein the first compound filled into the first chamber of the film bag consists of a silicone mixture which crosslinks sufficiently at room temperature, in order to be pre-crosslinked and dimensionally stable after few minutes of reaction time.

13. The method according to claim 1, wherein for complete crosslinking of the second compound filled into the second chamber of the film bag, a temperature is chosen such that the film permanently is plastically deformed without permanently damaging the film.

14. The method according to claim 1 wherein the films are a transparent, addition crosslinking two-component silicone rubber compound.

15. The method according to claim 1 wherein the fluid is air.

* * * * *